United States Patent
Romano et al.

(10) Patent No.: US 11,883,380 B2
(45) Date of Patent: *Jan. 30, 2024

(54) SULCARDINE ADMINISTRATION FOR TREATMENT OF ACUTE ATRIAL FIBRILLATION

(71) Applicant: HUYABIO International, LLC, San Diego, CA (US)

(72) Inventors: Suzanne J. Romano, Carlsbad, CA (US); Gary T. Elliott, Windsor, CO (US)

(73) Assignee: HUYABIO INTERNATIONAL, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,944

(22) Filed: May 23, 2022

(65) Prior Publication Data

US 2022/0280480 A1 Sep. 8, 2022

Related U.S. Application Data

(63) Continuation of application No. 16/712,677, filed on Dec. 12, 2019, now Pat. No. 11,364,223.

(60) Provisional application No. 62/858,324, filed on Jun. 6, 2019, provisional application No. 62/779,056, filed on Dec. 13, 2018.

(51) Int. Cl.
*A61K 31/4025* (2006.01)
*A61P 9/06* (2006.01)

(52) U.S. Cl.
CPC ............ *A61K 31/4025* (2013.01); *A61P 9/06* (2018.01)

(58) Field of Classification Search
None
See application file for complete search history.

(56) References Cited

U.S. PATENT DOCUMENTS

| | | | |
|---|---|---|---|
| 6,605,635 | B1 | 8/2003 | Bai et al. |
| 8,541,464 | B2 * | 9/2013 | Elliott ................ A61P 9/00 514/422 |
| 8,637,566 | B2 | 1/2014 | Elliott |
| 10,143,626 | B2 | 12/2018 | Li |
| 10,258,575 | B2 | 4/2019 | Li |
| 10,363,220 | B2 | 7/2019 | Li |
| 2012/0245214 | A1 | 9/2012 | Elliott |
| 2012/0309810 | A1 | 12/2012 | Elliott |
| 2019/0192440 | A1 | 6/2019 | Li |
| 2020/0316024 | A1 | 10/2020 | Romano et al. |
| 2021/0038568 | A1 | 2/2021 | Romano et al. |

FOREIGN PATENT DOCUMENTS

| | | |
|---|---|---|
| CN | 1939298 A | 4/2007 |
| WO | WO-2018/137686 A1 | 8/2018 |
| WO | WO-2020/123824 A1 | 6/2020 |

OTHER PUBLICATIONS

A Phase 1, randomised, double-blind, placebo-controlled, serial cohort dose-escalation study of intravenously administered HB1-3000. Clinicaltrials.gov study# NCT03397641 (2018).
"Abstracts from the 2009 Annual Meeting of the International Society for Heart Research North American Section: New Discoveries for Prevention and Treatment of Heart Disease," Baltimore, MD, United States. May 26, 2009-May 29, 2009. Journal of Molecular and Cellular Cardiology 46(5, Supp. 1) (2009).
"Huya Bioscience Int'l Announces First Pre-Ind Outcome for a Development Stage Compound Sourced From China—Hbi-8000, Promising New Cancer Compound," Apr. 14, 2008, retrieved from the internet: https://huyabio.com/huya-bioscience-intl-announces-first-pre-ind-outcome-development-stage-compound-sourced-china-hbi-8000-promising.new-cancer-compound/.
Bai et al., "Discovery of N-(3,5-bis(1-pyrrolidylmethyl)-4-hydroxybenzyl)-4-methoxybenzenesulfamide (sulcardine) as a novel anti-arrhythmic agent," ACTA Pharmacologica Sinica 33(9):1176-1186 (2012).
Berge, Stephen M., et al., "Pharmaceutical salts." Journal of pharmaceutical sciences 66.1 (1977): 1-19.
Chen et al., "Characteristics of hERG and hNav1 .5 channel blockade by sulcardine sulfate, a novel anti-arrhythmic compound," European Journal of Pharmacology 844, 2019, pp. 130-138.
Chen, Qian, et al. "Pharmacokinetics, safety, and tolerability of sulcardine sulfate: an open-label, single-dose, randomized study in healthy Chinese subjects." *Fundamental & clinical pharmacology* 31.1 (2017): 120-125.
"Guidance of Industry—Estimating the Maximum Safe Starting Dose in Initial Clinical Trials for Therapeutics in Adult Healthy Volunteers," U.S. Department of Health and Human Services, Pharmacology and Toxicology, Jul. 2005, 30 pages.
Guo et al., "Electrophysiologic Properties of HBI-3000: A New Antiarrhythmic Agent with Multiple-channel Blocking Properties in Human Ventricular Myocytes," Journal of Cardiovascular Pharmacology, vol. 57, No. 1, Jan. 2011, pp. 79-85.
Guo et al., "Electrophysiologic effect of HBI-3000: A novel antiarrhythmic compound with multiple channels blocking characteristics in human atrial and ventricular myocytes," Journal of Molecular and Cellular Cardiology 46(5, Supp. 1):S4-S5; abstract P-11 (2009).
Jia et al., "Determination of the novel antiarrhythmic drug sulcardine sulfate in human plasma by liquid chromatography tandem mass spectrometry and its application in a clinical pharmacokinetic study," Biomedical Chromatography 30(8), 2016, pp. 1291-1296.
Lapointe, et al., "Continuous intravenous quinidine infusion for the treatment of atrial fibrillation or flutter: A case series." American Heart Journal 139.1, Jan. 2000, pp. 114-121.
Lee at al., "HB1-3000 Prevents Secondary Sudden Cardiac Death," Journal of Cardiovascular Pharmacology and Therapeutics 18(5), 2013, pp. 453-459.
Lee et al., HB1-3000 Prevents Sudden Cardiac Death in a Conscious Canine Model., Cardiac Electro physiology Society, CES Annual Meeting. Chicago, IL, United States. Nov. 23, 2010-Nov. 13, 2010; Heart Rhythm 7(11), p. 1712.
Lee, et al., "Antifibrillatory actions of HBI-3000 in the conscious canine model of sudden cardiac death," *The FASEB Journal*, vol. 23, Issue 51, Apr. 1, 2009, pp. LB376-LB376.

(Continued)

*Primary Examiner* — Kamal A Saeed
(74) *Attorney, Agent, or Firm* — Eversheds Sutherland (US) LLP

(57) ABSTRACT

Provided herein are compositions and methods for administration of sulcardine to a subject in need thereof.

24 Claims, 5 Drawing Sheets

(56) References Cited

OTHER PUBLICATIONS

David C. Lee and Michael L. Webb, Pharmaceutical Analysis, Wiley-Blackwell, Feb. 2009, pp. 255-257.
Lu et al., "Oral Bioavailability and Mass Balance Studies of a Novel Anti-arrhythmic Agent Sulcardine Sulfate in Sprague-Dawley Rats and Beagle Dogs," European Journal of Drug Metabolism and Pharmacokinetics 42(3), 2017, pp. 453-459.
Mason, et al. "HBI-3000: A Novel Drug for Conversion of Atrial Fibrillation-Phase 1 Study Results." HUYA Bioscience International, Circulation 140, Suppl, 1, 2019, p. A11495.
"Drugs in Japan," Medicinal Drug Collection, Jiho Takeda, $27^{th}$ Edition, 2004, p. 2631, p. 2386.
PCT/US2019/066003 International Search Report and Written Opinion dated Mar. 20, 2020 (9 Pages).
PCT/US2020/015370 International Search Report and Written Opinion dated Jun. 6, 2020 (17 Pages).
PCT/US2020/015370 Invitation to Pay Additional Fees dated May 15, 2020 914 Pages).
Qi, et al., "Innovative drug R&D in China," Nature Reviews Drug Discovery, vol. 10, No. 5, May 2011, pp. 333-334.
Singh, et al., "N-Acylated sulfonamide sodium salt: A prodrug of choice for the bifunctional 2-hydroxymethyl-4-(5-phenyl-3-trifluoromethyl-pyrazol-1-yl) benzenesulfonamide class of COX-2 inhibitors," Bioorganic & Medicinal Chemistry Letters, vol. 16, May 11, 2006, pp. 3921-3926.
Streitwiesser et al., "Introduction to Organic Chemistry", Macmillan Publishing Co., 1992, p. 736.
Wang et al., "Multiple Dose Pharmacokinetics and Safety of Sulcardine Sulfate in Healthy Chinese Male Subjects: An Open-Label Phase I Clinical Study," European Journal of Drug Metabolism and Pharmacokinetics 42(4), 2017, pp. 593-599.
Wang, et al., "Effect of Sulcardine on cardiac electrophysiology in anesthetized rabbits," Chinese Pharmacological Society Communication vol. 19, No. 4, Nov. 4, 2002, pp. 63-64.
Wang, et al., "Electrophysiological Characterization of a Novel Artiarrhythmic Agent—Sulcardine Salts," AACTA Pharmacologica Sinica, Jul. 2006. vol. 27, Suppl. 1, p. 123.
Chinese Search Report for CN2010800519066, dated Jun. 13, 2014, (1 Page).
Japanese Decision of Refusal for JP2012-539070, drafted Apr. 2, 2015, (4 pages with English Translation).
Supplementary European Search Report for EP10832056, dated Apr. 22, 2013, (3 pages).
Japanese Decision of Refusal for JP2012-539071, drafted Apr. 22, 2015, (5 pages with English Translation).

* cited by examiner

Mean HBI-3000 Plasma Concentrations (of Sulcardine Free Base) Following a Single IV Infusion of 20, 60, 180, 360, or 600 mg HBI-3000

Concentration-ΔQTcF Model

Concentration-ΔHR Model

SULCARDINE ADMINISTRATION FOR TREATMENT OF ACUTE ATRIAL FIBRILLATION

CROSS-REFERENCE TO RELATED APPLICATIONS

This application is a Continuation of U.S. application Ser. No. 16/712,677, filed Dec. 19, 2019, which claims priority to U.S. Provisional Application Nos. 62/779,056, filed Dec. 13, 2018, and 62/858,324, filed Jun. 6, 2019, the entireties of which are incorporated herein by reference.

FIELD

The present teachings relate to compositions and methods for administration of sulcardine to a subject in need thereof.

BACKGROUND

U.S. Pat. Nos. 8,541,464 and 8,637,566 (each of which is incorporated herein by reference in its entirety) describe the activity of N-[4-hydroxy-3,5-bis(1-pyrrolidinylmethyl)benzyl]-4-methoxybenzenesulfonamide (hereinafter "sulcardine") and its pharmaceutically acceptable salts, in addition to various uses and methods of administering sulcardine in therapeutically effective amounts to subjects in need thereof.

Chen et al. reports the pharmacokinetics profiles of sulcardine in humans when administered orally. See Chen et al., "Pharmacokinetics, safety, and tolerability of sulcardine sulfate: an open-label, single-dose, randomized study in healthy Chinese subjects", *Fundamental & Clinical Pharmacology.* 31 (2017) 120-125.

There remains a need for developing formulations and methodology for alternative administration of sulcardine in humans to achieve different but desirable pharmacokinetic profiles.

SUMMARY

In one embodiment, provided herein are compositions for administering sulcardine in therapeutically effective amounts. In one embodiment, provided herein are compositions for enhanced and safer administration of sulcardine in therapeutically effective amounts.

In one embodiment, a pharmaceutical composition is provided comprising N-[4-hydroxy-3,5-bis(1-pyrrolidinylmethyl)benzyl]-4-methoxybenzenesulfonamide or a pharmaceutically acceptable salt thereof, wherein the composition produces a plasma profile characterized by a Cmax for the composition in a subject, after administering 600 mg of the composition, from about 5,000 ng/mL to about 6,000 ng/mL at about 0.5 hours after administration, and at most 25% of Cmax at about 1.0 hours after administration.

In one embodiment, a pharmaceutical composition is provided comprising N-[4-hydroxy-3,5-bis(1-pyrrolidinylmethyl)benzyl]-4-methoxybenzenesulfonamide or a pharmaceutically acceptable salt thereof, wherein the composition produces a plasma profile characterized by a Cmax for the compound in a subject, after administering 600 mg of the compound, from about 5,000 ng/mL to about 6,000 ng/mL at about 0.5 hours after administration, and at most 25% of Cmax at about 1.0 hours after administration.

In one embodiment, a pharmaceutical composition is provided comprising N-[4-hydroxy-3,5-bis(1-pyrrolidinylmethyl)benzyl]-4-methoxybenzenesulfonamide or a pharmaceutically acceptable salt thereof, wherein the composition displays desirable pharmacokinetic and pharmacodynamic effects, such as the ECG changes illustrated in the Example section.

Various methods can be accomplished using this composition.

In one embodiment, provided herein is a method of treating atrial fibrillation (AF), comprising intravenously administering to a human subject in need thereof sulcardine, or a pharmaceutically acceptable salt thereof, resulting in robust, albeit temporary, increase of QRS, PDur, PR, and TpTe, and reduction of JTp. In one embodiment, without being limited by a particular theory, these changes in ECG parameters are associated with rapid accumulation of the drug in the bloodstream through intravenous infusion combined with rapid inherent redistribution of the drug from the bloodstream and highly vascularized organs such as the heart to secondary compartments. Such a profile leads to rapid and significant changes in relevant ECG parameters associated with temporally linked cardioversion from atrial fibrillation to sinus rhythm followed by rapid reversal of ECG parameter changes upon drug redistribution, lessening risk of proarrhythmic events associated with QT, QRS and TpTe prolongation.

In one embodiment, provided herein is a method of treating atrial fibrillation (AF), comprising intravenously administering to a human subject in need thereof sulcardine, or a pharmaceutically acceptable salt thereof, at a dose of from about 60 mg to about 800 mg, in one embodiment from about 180 mg to about 800 mg, in one embodiment from about 200 mg to about 800 mg, and in one embodiment from about 400 mg to about 800 mg.

In one embodiment, provided herein is a method of treating atrial fibrillation (AF), comprising intravenously administering to a human subject in need thereof a therapeutically effective amount of sulcardine, or a pharmaceutically acceptable salt thereof, such that the plasma concentration of sulcardine in said human subject at the end of the administration is from about 1,400 ng/mL to about 8,000 ng/mL, and in one embodiment from about 4,000 ng/mL to about 8,000 ng/mL, and said plasma concentration of sulcardine decreases by at least about 75% within about 1 hour.

In various embodiments of compositions and methods provided herein, the pharmaceutically acceptable salt of sulcardine is sulcardine sulfate. In one embodiment, the pharmaceutically acceptable salt of sulcardine is sulcardine sulfate trihydrate.

These and other features, aspects and advantages of the present teachings will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

I. Definitions

Figure 1:
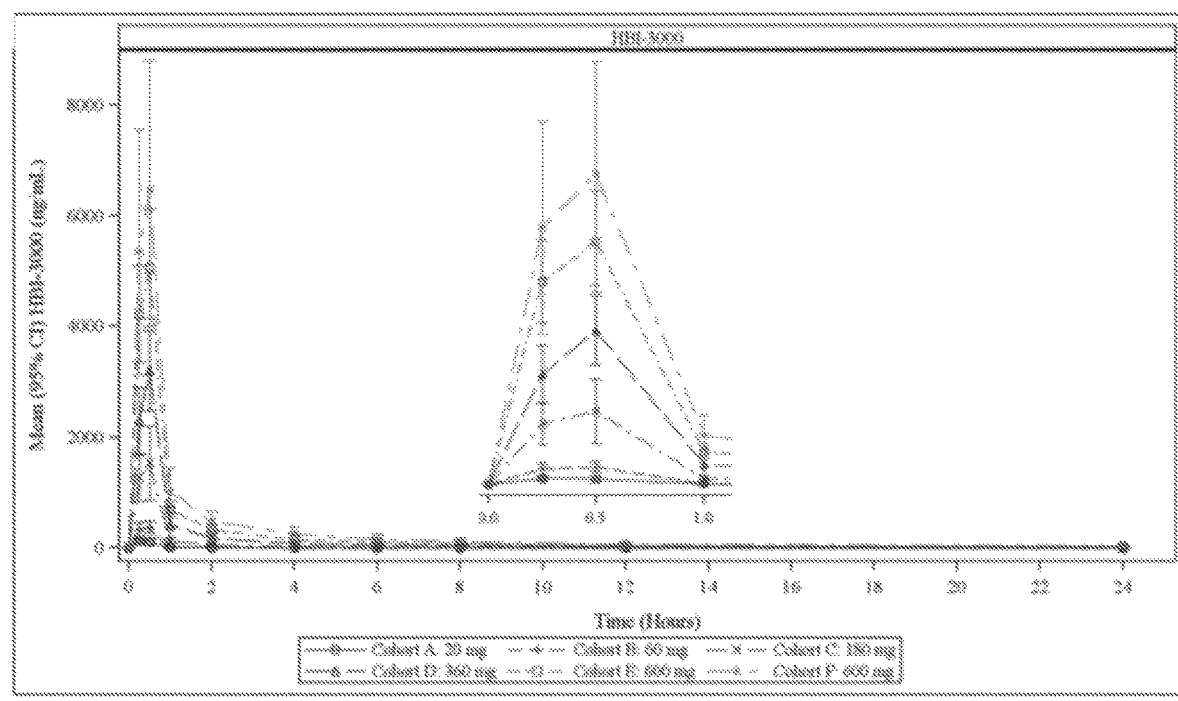
FIG. 1 is a graph depicting Mean (95% CI) sulcardine administered (ng/ml) on the Y-axis and Time (hours) on the X-axis. As depicted, sulcardine administered at a variety of dosages reaches peak plasma concentration (Cmax) at about 0.5 hours, and is largely removed or isolated from plasma at 1.0 hours.
Figure 2A:
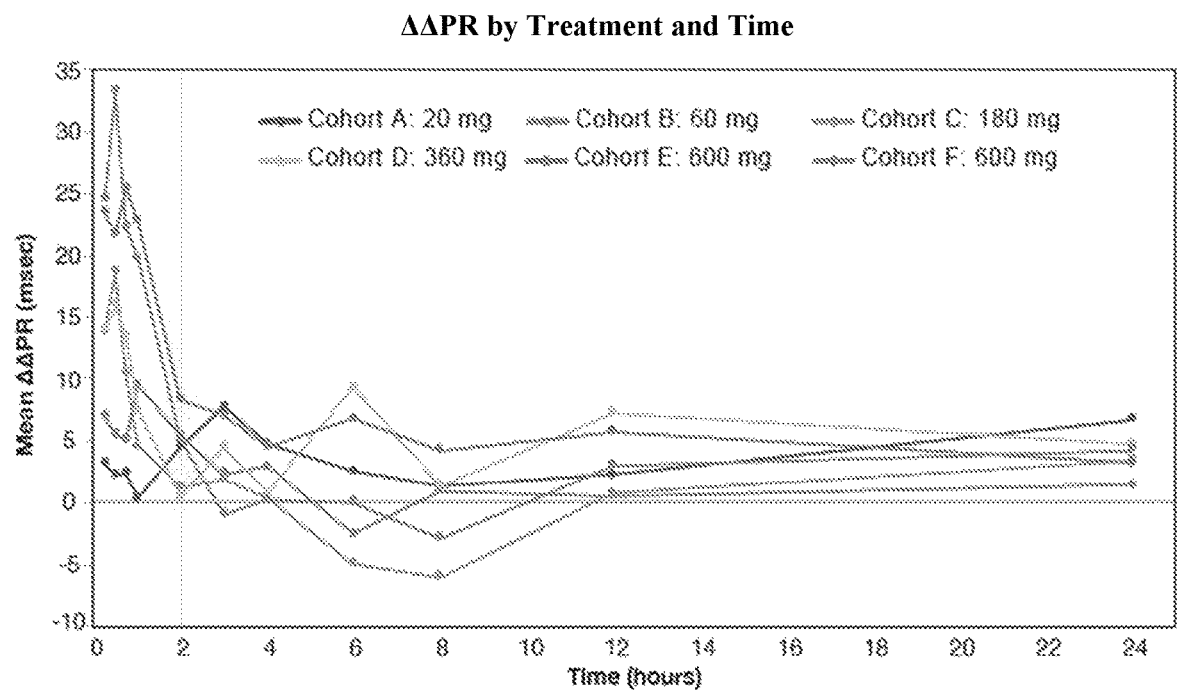
FIG. 2A, FIG. 2B, FIG. 2C, and FIG. 2D depict ΔΔPR, ΔΔQRS, ΔΔQTcF, and ΔΔHR, respectively, by treatment with sulcardine and time.
Figure 2B:
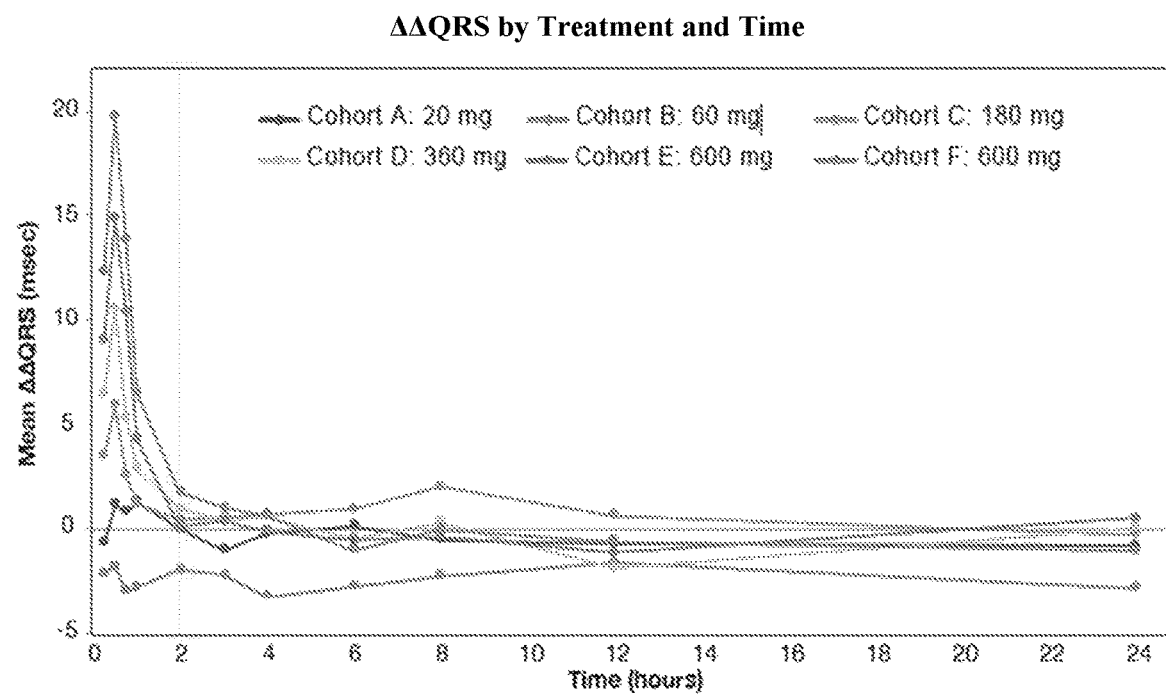
Figure 2C:
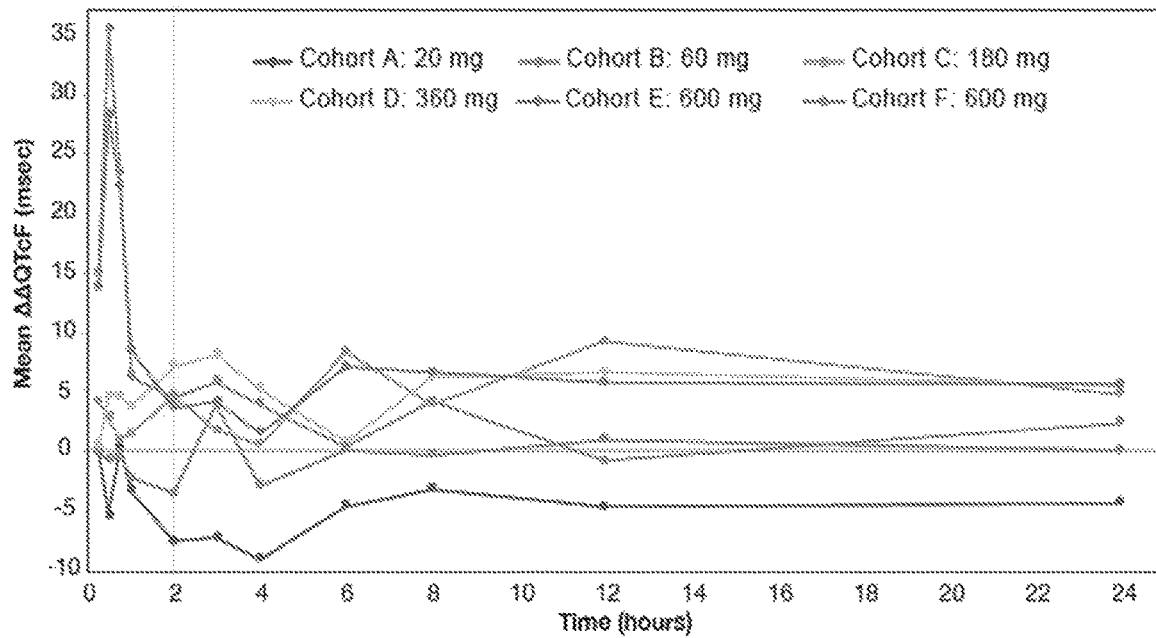
Figure 2D:
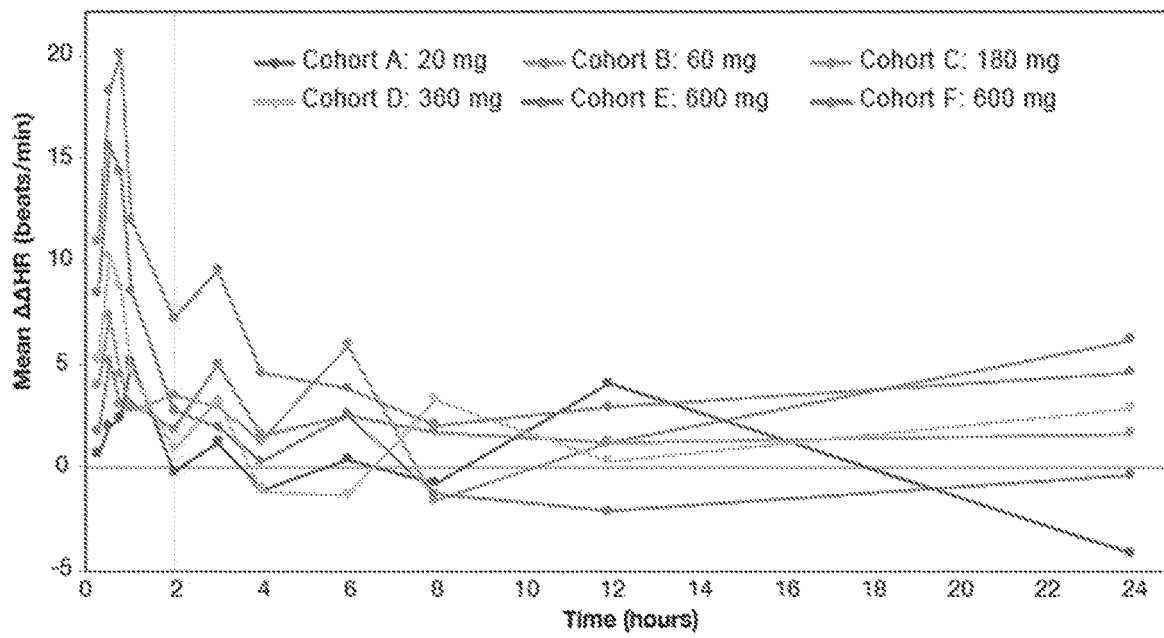
Figure 3A:
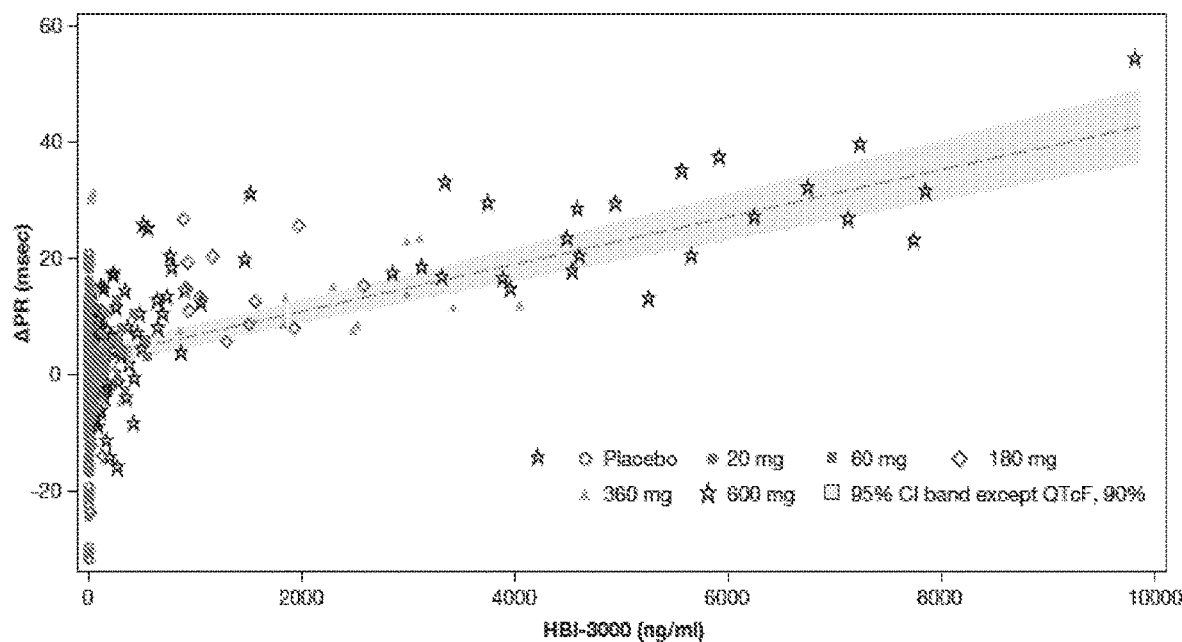
FIG. 3A, FIG. 3B, FIG. 3C, and FIG. 3D depict sulcardine concentration-effect relationship for ΔPR, ΔQRS, ΔQTcF, and ΔHR, respectively.
Figure 3B:
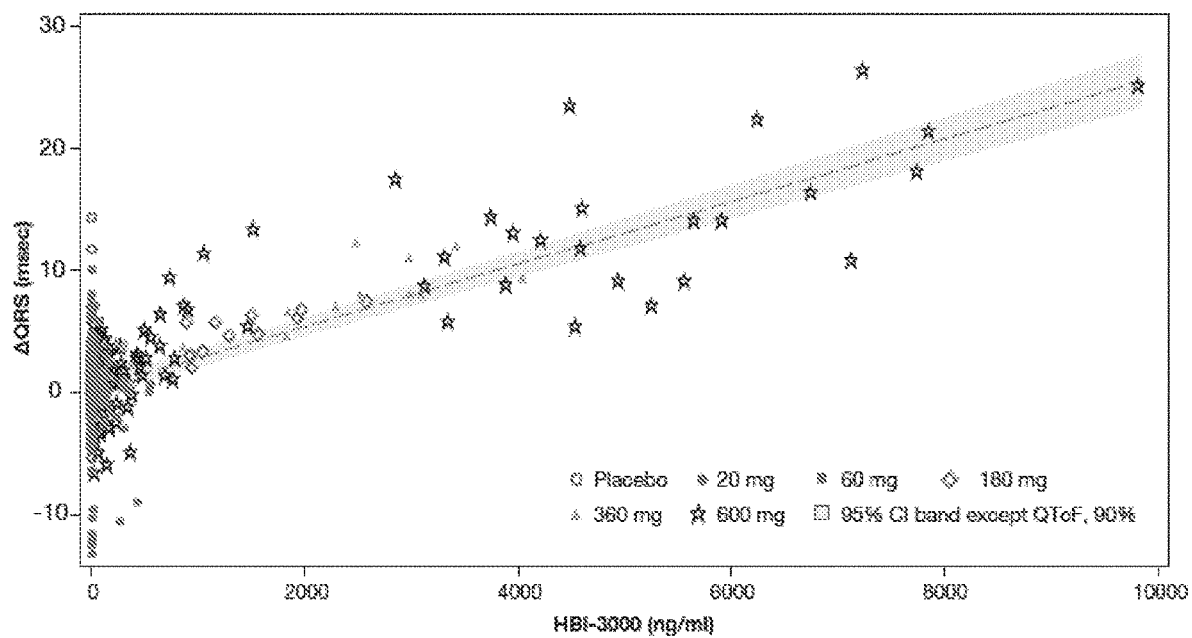
Figure 3C:
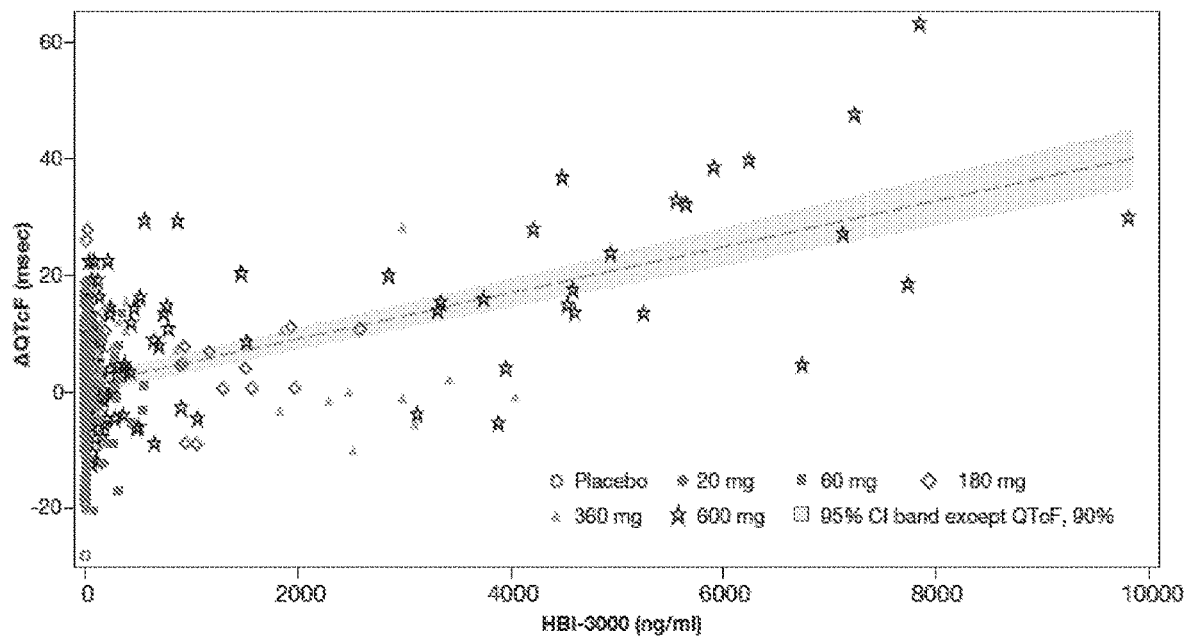
Figure 3D:
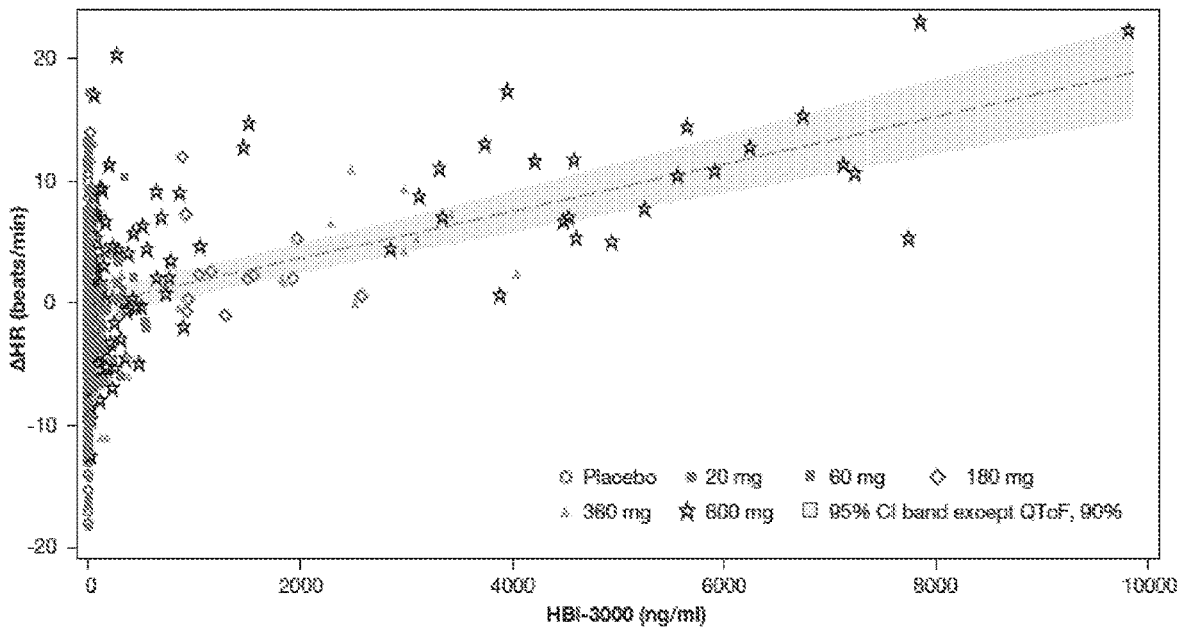

Unless indicated otherwise, the terms and phrases used in this description have the following meanings:

As used herein and unless otherwise specified, sulcardine has a chemical name of N-[4-hydroxy-3,5-bis(1-pyrrolidinylmethyl)benzyl]-4-methoxybenzenesulfonamide, and has the following structure:

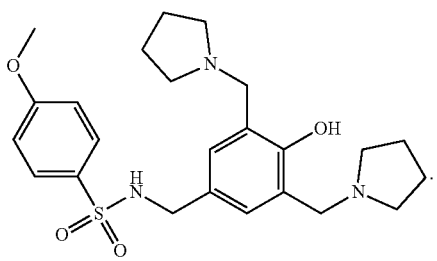 [SMILES: COc1ccc(S(=O)(=O)NCc2cc(CN3CCCC3)c(O)c(CN3CCCC3)c2)cc1]

As used herein and unless otherwise specified, sulcardine sulfate has the following structure:

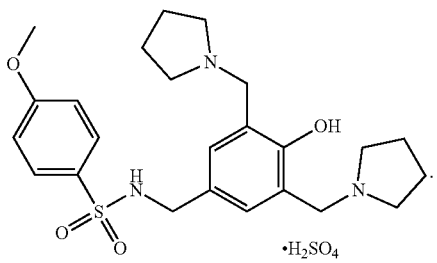

In one embodiment, the sulcardine sulfate is sulcardine sulfate trihydrate.

As used herein and unless otherwise specified, "Cmax" refers to maximum plasma concentration.

As used herein and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

"Treat," "treatment," and "treating" are employed in this description to refer to administering a pharmaceutical composition or formulation for prophylactic and/or therapeutic purposes. The term "therapeutic treatment" refers to administering treatment to a patient already suffering from a condition such as arrhythmia. Thus, in preferred embodiments, treating is the administration to a mammal of therapeutically effective amounts of an anti-arrhythmic agent.

A "subject" of treatment is a prokaryotic or a eukaryotic cell, a tissue culture, a tissue or an animal, e.g., a mammal, including a human. Non-human animals subject to treatment include, for example, a simian, a murine, a canine, a leporid, such as a rabbit, livestock, sport animals, and pets. As used herein and unless otherwise specified, a "patient" is a human subject.

An "anti-arrhythmic agent," as used herein, refers to a molecule having a therapeutic effect of treating arrhythmia or alleviating associated symptoms in a subject. Non-limiting examples of arrhythmias include supraventricular tachyarrhythmia such as atrial fibrillation, premature ventricular contractions, ventricular tachycardia, and ventricular fibrillation. In one aspect, an anti-arrhythmic agent is sulcardine, or a pharmaceutically acceptable salt thereof. In another aspect, an anti-arrhythmic agent is sulcardine sulfate.

As used herein, a pharmaceutically acceptable salt of sulcardine can be the active agent in a formulation useful for treating arrhythmia. Illustrative of such sulcardine salts are: (A) inorganic acid salts such as acetate, borate, bicarbonate, sulfate, hydrochloride, bromides, chlorides, iodide, hydrobromide, hydroiodide, nitrate, phosphate, diphosphate, and fluorophosphate salts; (B) organic acid salts such as amsonate (4,4-diaminostilbene-2,2-disulfonate), bitartrate, butyrate, citrate, calcium edetate, camsylate, edisylate, estolate, esylate, glutamate, gluconate, gluceptate, lactate, lactobionate, laurate, malate, maleate, mandelate, methylbromide, methylnitrate, methylsulfate, mucate, oleate, oxalate, palmitate, pamoate (1,1-methene-bis-2-hydroxy-3-naphthoate, einbonate), pamoate, pantothenate, salicylate, stearate, subacetate, succinate, sulfate, sulfosalicylate, suramate, propionate, valerate, fiunarate, fumarate, and tartrate salts; and (C) alkali metal salts and alkali earth salts, such as the sodium, potassium, lithium and calcium salts of sulcardine. In this context, a pharmaceutically acceptable salt can have more than one charged atom in its structure and, hence, one or more counterions.

The phrases "effective amount," "therapeutically effective amount," and "pharmaceutically effective amount" denote an amount of an active agent, such as an anti-arrhythmic agent as presently disclosed, that has a therapeutic effect. The doses of the active agent which are useful in treatment are therapeutically effective amounts. Thus, a therapeutically effective amount is an amount of the active agent that produces the desired therapeutic effect, as judged by clinical trial results and/or model animal studies. In particular embodiments, the active agent is administered in a predetermined dose; hence, a therapeutically effective amount would be an amount of the dose administered. This amount also can depend upon the patient's height, weight, sex, age and medical history.

A "carrier" or "excipient" is a compound or material used to facilitate administration of the compound, for example, to control the release and/or bioavailability of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); GOODMAN AND GILMAN'S: THE PHARMACOLOGICAL BASIS OF THERAPEUTICS, 8th Ed., Pergamon Press.

The phrases "pharmaceutically acceptable carrier" and "pharmaceutically acceptable excipient" can note any and all solvents, dispersion media, coatings, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. Suitable pharmaceutically acceptable excipients include, but are not limited to, buffers, diluents, tonicity agents, stabilizers, antioxidants, preservatives and mixtures thereof.

The term "buffer" denotes a pharmaceutically acceptable excipient, which stabilizes the pH of a pharmaceutical preparation. Suitable buffers are known in the art and can be found in the literature. Pharmaceutically acceptable buffers comprise but are not limited to glycine-buffers, histidine-buffers, citrate-buffers, succinate-buffers and phosphate-buffers. Independently from the buffer used, the pH can be adjusted at a value from about 2 to about 9, or alternatively from about 2.5 to about 7, or alternatively from about 3 to about 5 or alternatively about 3 with an acid or a base known in the art, e.g., succinic acid, hydrochloric acid, acetic acid, phosphoric acid, sulfuric acid and citric acid, sodium hydroxide and potassium hydroxide. Suitable buffers include, without limitation, glycine buffer, histidine buffer, 2-morpholinoethanesulfonic acid (MES), cacodylate, phosphate, acetate, succinate, and citrate. In one aspect, the buffer is a glycine buffer. In another aspect, the buffer is a histine buffer. The concentration of the buffer can be between about 1 mM and about 100 mM, or alternatively about 2 mM to about 40 mM, or alternatively about 5 mM to about 20 mM.

II. Method of Use

The goal of pharmacologic therapy for the treatment of AF depends on whether one is treating acute or paroxysmal AF, to induce rapid cardioversion to a normal sinus rhythm, or whether one seeks to prevent. AF recurrence with prolonged administration of the drug. In acute or paroxysmal AF in patients who do not have a history of frequent recurrence and perhaps to some extent in recurrent AF, although recurrent AF is more resistant to acute cardioversion by any means, the goal is to rapidly pharmacologically induce cardioversion of a patient who currently is suffering from an AF episode, typically with the administration of a single thug dose or with administration of a limited number of doses. Alternatively, prevention of recurrent AF episodes may require chronic prophylactic treatment.

In the context of treating acute or paroxysmal AF to induce immediate cardioversion, the efficacy of sulcardine and its pharmaceutically acceptable salts is believed to be a function of peak plasma concentration, requiring the maintenance of a high plasma level for a minimal period, for example, of minutes to less than one hour in duration, to afford time for cardioversion to a normal sinus rhythm after that time, the patient should remain in normal sinus rhythm without the need for continued therapeutic plasma levels of drug, unless some other precipitating event causes a future recurrence of the arrhythmia. These types of patients who have no or only limited prior history of AF episodes have lower risk of recurrence and are typically more successfully cardioverted regardless of the means of intervention; hence, continued drug therapy following cardioversion is not indicated. For the acute or paroxysmal AF indication, it is unnecessary to maintain steady blood levels of the drug (steady drug concentration area under the plasma-time curve) for prolonged periods of time. The use of the drug in this clinical situation is akin to the use of electrical cardioversion to acutely drive the heart back into a normal sinus rhythm.

The efficacy of sulcardine and its pharmaceutically acceptable salts in the treatment of patients with persistent or frequently recurring AF is thought to be a function of the area under the plasma-time curve, rather than of a peak plasma concentration. These patients, with a significant history of prior AF and frequent recurrence, are at much higher risk of recurrence that the acute cohort described above. The atria appear to remodel following frequent or prolonged (chronic) AF episodes, predisposing the patient to a higher risk of future events.

Prevention of recurrent AF or treatment of cardioverted chronic AF patients requires maintaining drug concentration peak and trough concentrations over the dosing period within a range that minimizes the risk of adverse events, associated with high plasma concentrations, and yet that maintains blood levels above some minimally pharmacologically active concentration. Accordingly, in the treatment of recurrent or chronic cardioverted AF patients, administering active agent over a longer period, e.g., by means of a controlled release formulation or by slow intravenous infusion, has a role to play. In the acute/paroxysmal AF medical setting, the goal is to achieve rather high blood levels for a period of minutes out to an hour or two, allowing the heart sufficient time to respond to drug therapy and slip back into a normal sinus rhythm. Loading the drug by a continuous, short-term infusion over this period, as opposed to administering the drug by a rapid IV push, blunts peak plasma concentrations, minimizing the risk of hypotension which can occur with antiarrhythmic agents that possess activity at $I_{Ca}$ calcium ion channel or which possess a vagolytic effect, while allowing for the achievement of high blood levels over a period of time sufficient to result in cardioversion.

Provided herein are compositions and methods for administration of sulcardine, or a pharmaceutically acceptable salt thereof, in a subject which allows for a pharmacokinetic/pharmacodynamics (PK/PD) profile suitable for treating AF, e.g., acute or paroxysmal AF. In one embodiment, without being limited by a particular theory, the PK/PD profile is achieved by one or more of the following factors: IV administration for fast $T_{max}$ and high $C_{max}$; rapid redistribution to lower arrythmia risk; pan-electrophysiologic effect on ECG; and opposing QTc/TpTe and jTp profile presenting lower TdeP risk. In one embodiment, without being limited by a particular theory, it is also surprisingly discovered that sulcardine, or a pharmaceutically acceptable salt thereof, can be administered at certain dosages and in a certain route which are quickly effective when measured using certain pharmacokinetic and pharmacodynamics parameters, but also lose effect quickly. Therefore, sulcardine, or a pharmaceutically acceptable salt thereof, can be more safely and effectively administered to subjects using specific dosages, and a specific route of administration, which will also result in beneficial outcomes.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces pan-ECG parameter changes including:

increases in QRS, PDur, PR, and QTcF; reduction of JTp; and no effect or increase in TpTe.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces dose proportional ECG parameter changes including:
increases in QRS, PDur, PR, QTcF; reduction of JTp; and no effect or increase in TpTe.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces dose proportional ECG parameter changes including:
increases in QRS, PDur, PR, and TpTe.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces dose proportional ECG parameter changes including:
reduction of JTp.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces dose proportional ECG parameter changes including:
no effect or prolonged TpTe interval.

In one embodiment, the administration range is from 20 to 1000 mg. In one embodiment, the range is from 20 to 600 mg. In one embodiment, the range is from 60 to 600 mg.

In one embodiment, the pharmaceutically acceptable salt in the composition is sulcardine sulfate.

In one embodiment, provided herein is a method of administering a composition provided herein to a subject in need thereof, wherein a panoply of ECG parameters are changed in the subject. In one embodiment, QRS, PDur, PR, and TpTe are increased in the subject, and JTp is reduced in the subject.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces a plasma profile characterized by a Cmax for the composition in a subject, after administering 600 mg of the composition, from about 5,000 ng/mL to about 6,000 ng/mL at about 0.5 hours after administration, and at most 25% of Cmax at about 1.0 hours after administration.

In one embodiment, provided herein is a pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces a plasma profile characterized by a Cmax for the compound in a subject, after administering 600 mg of the compound, from about 5,000 ng/mL to about 6,000 ng/mL at about 0.5 hours after administration, and at most 25% of Cmax at about 1.0 hours after administration.

In one embodiment, the pharmaceutically acceptable salt in the composition is sulcardine sulfate.

In one embodiment, the composition produces a change in QT that does not deviate by more than about 40 msec after administering between about 20 mg and 600 mg of the composition to the subject.

In one embodiment, provided herein is a method of administering a composition provided herein to a subject in need thereof, whereby the composition produces a plasma profile characterized by a Cmax for the composition in a subject, after administering 600 mg of the composition, from about 5,000 ng/mL to about 6,000 ng/mL at about 0.5 hours after administration, and at most 25% of Cmax at about 1.0 hours after administration.

In one embodiment, provided herein is a method of administering a composition provided herein to a subject in need thereof, whereby the composition produces a plasma profile characterized by a Cmax for the compound (sulcardine) in a subject, after administering 600 mg of the compound, from about 5,000 ng/mL to about 6,000 ng/mL at about 0.5 hours after administration, and at most 25% of Cmax at about 1.0 hours after administration.

In one embodiment, the pharmaceutical composition provided herein further comprises a pharmaceutically acceptable excipient.

In one embodiment, provided herein is a method of treating atrial fibrillation (AF), comprising intravenously administering to a human subject in need thereof sulcardine, or a pharmaceutically acceptable salt thereof, resulting in pan-ECG parameter changes including increases in QRS, PDur, PR, TpTe, and QTcF, and reduction of JTp.

In one embodiment, provided herein is a method of treating atrial fibrillation (AF), comprising intravenously administering to a human subject in need thereof sulcardine, or a pharmaceutically acceptable salt thereof, resulting in increase of QRS, PDur, PR, and TpTe, and reduction of JTp.

In one embodiment, sulcardine, or a pharmaceutically acceptable salt thereof, is administered at a dose range of from about 20 to about 1000 mg. In one embodiment, sulcardine, or a pharmaceutically acceptable salt thereof, is administered at a dose range of from about 20 to about 600 mg. In one embodiment, sulcardine, or a pharmaceutically acceptable salt thereof, is administered at a dose range of from about 60 to about 600 mg.

In one embodiment, provided herein is a method of treating atrial fibrillation (AF), comprising intravenously administering to a human subject in need thereof sulcardine, or a pharmaceutically acceptable salt thereof, at a dose of from about 60 mg to about 800 mg. In one embodiment, the dose is from about 100 mg to about 800 mg. In one embodiment, the dose is from about 200 mg to about 800 mg. In one embodiment, the dose is from about 400 mg to about 800 mg.

In one embodiment, the QT interval in said human subject is increased by from about no more than 40 msec at the end of the administration. In one embodiment, the QT interval in said human subject is increased by from about 10 msec to about 40 msec at the end of the administration. In one embodiment, the QT interval in said human subject is increased by from about 20 msec to about 30 msec at the end of the administration.

In one embodiment, provided herein is a method of treating atrial fibrillation (AF), comprising intravenously administering to a human subject in need thereof a therapeutically effective amount of sulcardine, or a pharmaceutically acceptable salt thereof, such that the plasma concentration of sulcardine in said human subject at the end of the administration is from about 370 ng/mL to about 8,000 ng/mL, and said plasma concentration of sulcardine decreases by at least about 75% within about 1 hour.

In one embodiment, the plasma concentration of sulcardine in said human subject at the end of the administration is from about 1,400 ng/mL to about 8,000 ng/mL. In one embodiment, the plasma concentration of sulcardine in said human subject at the end of the administration is from about 2,000 ng/mL to about 8,000 ng/mL. In one embodiment, the plasma concentration of sulcardine in said human subject at the end of the administration is from about 5,000 ng/mL to about 6,000 ng/mL.

In one embodiment, sulcardine, or a pharmaceutically acceptable salt thereof, is administered at a dose of from about 60 mg to about 800 mg. In one embodiment, sulcardine, or a pharmaceutically acceptable salt thereof, is administered at a dose of from about 180 mg to about 800 mg. In one embodiment, sulcardine, or a pharmaceutically acceptable salt thereof, is administered at a dose of from about 360 mg to about 800 mg. In one embodiment, sulcardine, or a pharmaceutically acceptable salt thereof, is administered at a dose of from about 400 mg to about 800 mg. In one embodiment, sulcardine, or a pharmaceutically acceptable salt thereof, is administered at a dose of from about 450 mg to about 750 mg. In one embodiment, sulcardine, or a pharmaceutically acceptable salt thereof, is administered at a dose of from about 500 mg to about 700 mg. In one embodiment, sulcardine, or a pharmaceutically acceptable salt thereof, is administered at a dose of from about 550 mg to about 650 mg. In one embodiment, sulcardine, or a pharmaceutically acceptable salt thereof, is administered at a dose of about 600 mg.

In one embodiment, sulcardine, or a pharmaceutically acceptable salt thereof, is administered at a dose of no less than about 60 mg. In one embodiment, sulcardine, or a pharmaceutically acceptable salt thereof, is administered at a dose of no less than about 180 mg. In one embodiment, sulcardine, or a pharmaceutically acceptable salt thereof, is administered at a dose of no less than about 360 mg. In one embodiment, sulcardine, or a pharmaceutically acceptable salt thereof, is administered at a dose of no less than about 400 mg. In one embodiment, sulcardine, or a pharmaceutically acceptable salt thereof, is administered at a dose of no less than about 450 mg. In one embodiment, sulcardine, or a pharmaceutically acceptable salt thereof, is administered at a dose of no less than about 500 mg. In one embodiment, sulcardine, or a pharmaceutically acceptable salt thereof, is administered at a dose of no less than about 550 mg. In one embodiment, sulcardine, or a pharmaceutically acceptable salt thereof, is administered at a dose of no less than about 600 mg. In one embodiment, sulcardine, or a pharmaceutically acceptable salt thereof, is administered at a dose of no less than about 650 mg. In one embodiment, sulcardine, or a pharmaceutically acceptable salt thereof, is administered at a dose of no less than about 700 mg. In one embodiment, sulcardine, or a pharmaceutically acceptable salt thereof, is administered at a dose of no less than about 750 mg. In one embodiment, sulcardine, or a pharmaceutically acceptable salt thereof, is administered at a dose of no less than about 800 mg.

In one embodiment, sulcardine, or a pharmaceutically acceptable salt thereof, is administered at a dose of about 60 mg. In one embodiment, sulcardine, or a pharmaceutically acceptable salt thereof, is administered at a dose of about 180 mg. In one embodiment, sulcardine, or a pharmaceutically acceptable salt thereof, is administered at a dose of about 360 mg. In one embodiment, sulcardine, or a pharmaceutically acceptable salt thereof, is administered at a dose of about 400 mg. In one embodiment, sulcardine, or a pharmaceutically acceptable salt thereof, is administered at a dose of about 450 mg. In one embodiment, sulcardine, or a pharmaceutically acceptable salt thereof, is administered at a dose of about 500 mg. In one embodiment, sulcardine, or a pharmaceutically acceptable salt thereof, is administered at a dose of about 550 mg. In one embodiment, sulcardine, or a pharmaceutically acceptable salt thereof, is administered at a dose of about 600 mg. In one embodiment, sulcardine, or a pharmaceutically acceptable salt thereof, is administered at a dose of about 650 mg. In one embodiment, sulcardine, or a pharmaceutically acceptable salt thereof, is administered at a dose of about 700 mg. In one embodiment, sulcardine, or a pharmaceutically acceptable salt thereof, is administered at a dose of about 750 mg. In one embodiment, sulcardine, or a pharmaceutically acceptable salt thereof, is administered at a dose of about 800 mg.

In one embodiment, the dosages of sulcardine may also include about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, and dosage in between. The dosages may also include about 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, and dosages in between. The dosages of sulcardine may also include about 850 mg, 900 mg, 950 mg and 1,000 mg if it can be shown that such dosages are both safe and have the intended effect.

In one embodiment, sulcardine, or a pharmaceutically acceptable salt thereof, is administered at a dose of about 60 mg, 180 mg, about 360 mg, or about 600 mg, and dosages in between. In one embodiment, sulcardine, or a pharmaceutically acceptable salt thereof, is administered at a dose of from about 180 mg to about 600 mg.

In one embodiment, a pharmaceutically acceptable salt of sulcardine is administered. In one embodiment, sulcardine sulfate is administered.

In one embodiment, sulcardine, or a pharmaceutically acceptable salt thereof, is administered as a solution with a concentration of about 50 mg/mL. In one embodiment, the solution is diluted to about 8 mg/ml or less to deliver about 200-500 mg dose in a volume of 50 ml to a patient.

In one embodiment, sulcardine, or a pharmaceutically acceptable salt thereof, is administered over a period of from about 15 minutes to about 2 hours. In one embodiment, sulcardine, or a pharmaceutically acceptable salt thereof, is administered over a period of from about 30 minutes to about 1 hour. In one embodiment, sulcardine, or a pharmaceutically acceptable salt thereof, is administered over a period of about 30 minutes.

In one embodiment, the AF is acute AF.
In one embodiment, the AF is paroxysmal AF.
In one embodiment, the AF is recurrent AF.

III. Examples

Aspects of the present disclosure may be further understood in light of the following examples, which should not be construed as limiting the scope of the present disclosure in any way.

Example 1—Administration of Sulcardine

HBI-3000 (sulcardine sulfate) was administered to human subjects according to the protocol provided in ClinicalTrials.gov Identifier: NCT03397641. That protocol is incorporated herein by reference in its entirety.

Background: HBI-3000 is a multi-ion channel blocker with relatively balanced in vitro inhibitory effects on $I_{Na-Peak}$, $I_{Na-Late}$, $I_{Ca,L}$ and $I_{Kr}$ being developed by HUYA Bioscience International for the conversion of recent onset atrial fibrillation (AF).

Objective: Provided herein are the safety, tolerability, pharmacokinetics and electrocardiogram (ECG) results of a Phase 1 single ascending dose trial of intravenous (iv) HBI-3000 in healthy subjects. Selected ECG parameters and abbreviations are shown in Table 1.

TABLE 1

ECG parameters and abbreviations

| Parameter | ECG Variable | Baseline Corrected ECG Variable (ΔECG) | Baseline and Pooled Placebo Corrected ECG Variable (ΔΔECG) |
|---|---|---|---|
| Heart rate, bpm | HR | ΔHR | ΔΔHR |
| PR interval, msec | PR | ΔPR | ΔΔPR |
| P-wave duration, msec | PDur | ΔPDur | ΔΔPDur |
| QRS interval, msec | QRS | ΔQRS | ΔΔQRS |
| Fridericia-corrected QT interval, msec | QTcF | ΔQTcF | ΔΔQTcF |
| J to T peak interval, msec | JTp | ΔJTp | ΔΔJTp |
| T peak to T end interval, msec | TpTe | ΔTpTe | ΔΔTpTe |

Methods: Forty-seven subjects were randomized to 6 cohorts of 8 subjects to receive 1 of 5 single ascending iv doses (Table 2) of HBI-3000 or placebo (6:2), with 2 cohorts receiving the 600 mg dose. Doses of HBI-3000 ranged from 20 mg (Cohort A), 60 mg (Cohort B), 180 mg (Cohort C), 360 mg (Cohort D), to 600 mg (Cohort E and F). Drug was a lyophilized powder, reconstituted to 50 ml/ml then diluted in saline for delivery via intravenous infusion as a 50 mL solution over 30 minutes.

Continuous 12-lead Holter ECG data were recorded at baseline and 11 time points thereafter. Mean baseline and placebo subtracted (ΔΔ) ECG intervals (QTcF, HR, PR, QRS, and P-wave duration [PDur]) and T-wave segments (J to T peak [JTp] and T peak to T end [TpTe]) were calculated at Cmax for each dose.

Results: HBI-3000 was well tolerated with no dose limiting adverse events or arrhythmias observed.

Table 2 summarizes ECG data at Cmax for each dose, as predicted by mixed-effects modeling. HBI-3000 induced dose-proportional changes in all ECG parameters. The increases in QRS and PDur are consistent with block of $I_{Na-peak}$. The increase in the PR interval is consistent with the increase in PDur and with both $I_{Na-Peak}$ and $I_{Ca,L}$ inhibition. Prolongation of TpTe is consistent with $I_{Kr}$ block, which would be expected, in isolation, to lengthen JTp as well. The observed dose-related reduction of JTp is likely due to counteraction of the effect of HBI-3000 on $I_{Kr}$ through its inhibition of both $I_{Na-Late}$, and $I_{Ca-L}$.

TABLE 2

ΔΔECG by Dose from Concentration-Effect Regression Model

| Mean, msec or bpm | ΔΔQTcF | ΔΔHR | ΔΔPR | ΔΔQRS | ΔΔPDur | ΔΔJTp | ΔΔTpTe |
|---|---|---|---|---|---|---|---|
| Dose, Cmax (N) | | | | | | | |
| 20 mg, 135 ng/ml (6) | 1.40 | 1.74 | 5.08 | −0.08 | 3.17 | −2.87 | 1.95 |
| 60 mg, 378 ng/ml (6) | 2.35 | 2.21 | 6.06 | 0.54 | 3.71 | −5.28 | 2.20 |
| 180 mg, 1530 ng/ml (6) | 6.89 | 4.44 | 10.73 | 3.50 | 6.24 | −15.09 | 3.37 |
| 360 mg, 3120 ng/ml (5) | 13.50 | 7.70 | 17.53 | 7.81 | 9.93 | −24.60 | 5.07 |
| 600 mg, 5280 ng/ml (12) | 23.77 | 12.75 | 28.10 | 14.50 | 15.67 | −28.10 | 7.72 |
| Slope | 0.0039 | 0.0019 | 0.0040 | 0.0026 | 0.0022 | −0.0000 | 0.0010 |
| P value | <0.0001 | <0.0001 | <0.0001 | <0.0001 | <0.001 | <0.0001 | <0.0001 |

Table 3 shows selected pharmacokinetic data for each dose.

TABLE 3

Selected Pharmacokinetic Data

| Dose of HBI-3000 | N | Tmax Mean (h) (Min-Max) | Cmax (ng/mL) (G. CV (%)) | AUC (0-24) (ng · h/mL) (G. CV (%)) | AUC (0-last) (ng · h/mL) (G. CV (%)) | AUC (0-inf) (ng · h/mL) (G. CV (%)) | T½ (h) (G. CV (%)) |
|---|---|---|---|---|---|---|---|
| 20 mg | 6 | 0.42 (0.25-0.52) | 131 (29.60) | 89.7 (53.00) | 86.2 (54.80) | 175 (NC) | 0.62 (NC) |
| 60 mg | 6 | 0.38 (0.25-0.52) | 369 (23.80) | 299 (17.40) | 306 (18.30) | 312 (NC) | 9.16 (NC) |
| 180 mg | 6 | 0.46 (0.25-0.50) | 1430 (41.60) | 1270 (25.60) | 1550 (23.00) | 2050 (41.80) | 54.76 (32.8) |
| 360 mg | 5 | 0.45 (0.27-0.50) | 3170 (17.60) | 2960 (23.70) | 3470 (26.60) | 3830 (33.80) | 43.68 (48.9) |
| 600 mg | 12 | 0.46 (0.25-0.50) | 5580 (30.50) | 5810 (31.20) | 6640 (30.50) | 7580 (28.90) | 41.14 (20.7) |

Additional finding: when sulcardine sulfate is administered at certain dosages, the compound not only becomes pharmacodynamically active in human subjects, but also becomes quickly ineffective. In other words, the compound may be administered in certain dosages which results in quick effects in the subject, and then the compound is no longer effective on the cardiovascular system of the subject. It is unknown by what route the compound is removed from or isolated from the cardiovascular system so that it is not effective. However, it has been discovered that when sulcardine sulfate is administered in an amount from about 400 mg to about 800 mg according to the protocol above, the compound is quickly effective and then quickly loses its effect. Those of skill in the art will recognize that these effects may further enhance the safety profile of the compound whereby certain dosages, and/or dosage forms, may be prepared and administered which avoid unwanted side effects.

As shown in FIG. 1, when sulcardine sulfate was administered at various dosages, the compound reached Cmax in approximately 0.5 hours, and then was quickly removed or isolated from plasma. This effect occurred in a range of dosages from about 180 mg to about 600 mg. What is unexpected is that administration produced a quick change in ECG parameters and then the subject quickly returned to steady state (FIG. 2A, FIG. 2B, FIG. 2C, and FIG. 2D). Similar to an "on/off" switch, the effect of sulcardine sulfate administration appears and then disappears within an unexpectedly short amount of time.

The concentration-dECG model combining all doses of HBI-3000 are displayed in FIG. 3A, FIG. 3B, FIG. 3C, and FIG. 3D. The one sided 95% confidence interval around the HBI-3000 slope is represent by the light band.

Conclusions: These data demonstrate that RBI-3000 is a potent inhibitor of multiple cardiac ion channels that play a role in onset and maintenance of AF. Its strong reduction of JTp may predict freedom from arrhythmias associated with $I_{Kr}$ block. Based on these results and preclinical data indicating low proarrhythmic risk, the drug is now entering Phase 2 in recent onset AF.

Those of skill in the art will also recognize various methods of determining the plasma concentration of sulcardine in a patient at any point in time via enzyme linked assays, including ELISA. Such methods are useful in determining whether the Cmax has been reached in a subject, and when administration of sulcardine may be terminated.

Considering that the expected half-life for oral administration of sulcardine is about 16 hours (See Chen et al., *Fundamental & Clinical Pharmacology*. 31 (2017) 120-125), it was surprising that the present formulation administered as provided herein resulted in the quick "on/off" profile. Such unexpected results provide an opportunity for more safely providing the intended effects of sulcardine administration as provided in U.S. Pat. Nos. 8,541,464 and 8,637,566. In addition, unlike Chen et al. whereby sulcardine is slowly re-distributed in a subject, it is surprising that the rapid re-distribution of sulcardine in a subject as formulated and administered in the present invention re-distributes quickly. This also provides an avenue for more safely administering sulcardine, and reducing pro-arrhythmic risk.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A pharmaceutical composition comprising a compound, which is N-[4-hydroxy-3,5-bis(1-pyrrolidinylmethyl)benzyl]-4-methoxybenzenesulfonamide or a pharmaceutically acceptable salt thereof, wherein the composition produces pan-ECG parameter changes including:
   increase in QRS, PDur, PR, and QTcF or reduction of JTp; and no effect on TpTe or increase in TpTe.

2. The pharmaceutical composition of claim 1, wherein the composition is administered to a subject at a dose of from about 20 to 1000 mg to produce the ECG parameter changes.

3. The pharmaceutical composition of claim 2, wherein the dose is from 20 to 600 mg.

4. The pharmaceutical composition of claim 1, wherein the pharmaceutically acceptable salt is represented by the formula:

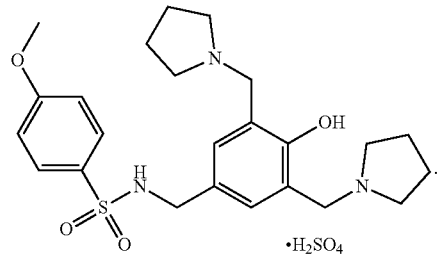

5. The composition of claim 1, whereby QRS, PDur, PR, TpTe, and QTcF are increased in the subject, and JTp is reduced in the subject.

6. The pharmaceutical composition of claim 1 upon administering 600 mg of the compound, produces a plasma profile characterized by a Cmax for the compound in the subject, from about 5,000 ng/ml to about 6,000 ng/ml at about 0.5 hours after administration, and wherein at most 25% of Cmax is reached at about 1.0 hours after administration.

7. The pharmaceutical composition of claim 3, wherein the composition produces a change in QT that does not deviate by more than about 40 msec after administering between about 20 mg and 600 mg of the composition to the subject.

8. A method of treating atrial fibrillation (AF), comprising intravenously administering to a human subject in need thereof sulcardine, or a pharmaceutically acceptable salt thereof, resulting in increase in QRS, PDur, PR, and QTcF, and reduction of JTp, and no effect or increase in TpTe.

9. The method of claim 8, wherein sulcardine, or a pharmaceutically acceptable salt thereof, is administered at a dose range of from about 20 to about 1000 mg.

10. The method of claim 9, wherein sulcardine, or a pharmaceutically acceptable salt thereof, is administered at a dose range of from about 20 to about 600 mg.

11. The method of claim 9, comprising intravenously administering to a human subject in need thereof sulcardine, or a pharmaceutically acceptable salt thereof, at a dose of from about 60 mg to about 800 mg.

12. The method of treating atrial fibrillation (AF), comprising intravenously administering to a human subject in need thereof a therapeutically effective amount of sulcardine, or a pharmaceutically acceptable salt thereof, such that the plasma concentration of sulcardine in said human subject at the end of the administration is from about 370 ng/ml to about 8,000 ng/ml, and said plasma concentration of sulcardine decreases by at least about 75% within about 1 hour.

13. The method of claim 12, wherein the plasma concentration of sulcardine in said human subject at the end of the administration is from about 5,000 ng/ml to about 6,000 ng/mL.

14. The method of claim 9, wherein sulcardine, or a pharmaceutically acceptable salt thereof, is administered at a dose of from about 400 mg to about 800 mg.

15. The method of claim 14, wherein sulcardine, or a pharmaceutically acceptable salt thereof, is administered at a dose of from about 500 mg to about 700 mg.

16. The method of claim 15, wherein sulcardine, or a pharmaceutically accept able salt thereof, is administered at a dose of about 600 mg.

17. The method of claim 8, wherein a pharmaceutically acceptable salt of sulcardine is administered.

18. The method of claim 17, wherein sulcardine sulfate is administered.

19. The method of claim 8, wherein sulcardine, or a pharmaceutically acceptable salt thereof, is administered over a period of from about 15 minutes to about 2 hours.

20. The method of claim 19, wherein sulcardine, or a pharmaceutically acceptable salt thereof, is administered over a period of from about 30 minutes to about 1 hour.

21. The method of claim 20, wherein sulcardine, or a pharmaceutically acceptable salt thereof, is administered over a period of from about 30 minutes.

22. The method of claim 8, wherein the AF is acute AF.

23. The method of claim 8, wherein the AF is paroxysmal AF.

24. The method of claim 8, wherein the AF is recurrent AF.

* * * * *